(12) United States Patent
Jadhav et al.

(10) Patent No.: US 10,537,105 B2
(45) Date of Patent: Jan. 21, 2020

(54) STABLE AQUEOUS COMPOSITIONS

(71) Applicant: UPL Limited, Mumbai (IN)

(72) Inventors: Prakash Mahadeo Jadhav, Lawrenceville, NJ (US); Mark William Weber, Conshohocken, PA (US); Vikram Rajnikant Shroff, Mumbai (IN)

(73) Assignee: UPL Limited, Mumbai (IN)

( * ) Notice: Subject to any disclaimer, the term of this patent is extended or adjusted under 35 U.S.C. 154(b) by 0 days.

(21) Appl. No.: 15/040,722

(22) Filed: Feb. 10, 2016

(65) Prior Publication Data

US 2016/0235071 A1    Aug. 18, 2016

Related U.S. Application Data

(60) Provisional application No. 62/114,325, filed on Feb. 10, 2015.

(51) Int. Cl.
| | |
|---|---|
| *A01N 57/20* | (2006.01) |
| *A01N 43/88* | (2006.01) |
| *A01N 25/22* | (2006.01) |
| *A01N 37/48* | (2006.01) |

(52) U.S. Cl.
CPC ............. *A01N 57/20* (2013.01); *A01N 37/48* (2013.01); *A01N 43/88* (2013.01)

(58) Field of Classification Search
CPC ........ A01N 43/88; A01N 25/02; A01N 25/30; A01N 37/48
See application file for complete search history.

(56) References Cited

U.S. PATENT DOCUMENTS

| | | | | |
|---|---|---|---|---|
| 5,541,152 A | * | 7/1996 | Lehs ...................... | A01N 25/32 504/110 |
| 2012/0322661 A1 | * | 12/2012 | Shroff .................... | A01N 25/04 504/333 |
| 2014/0213656 A1 | * | 7/2014 | Tokubuchi .............. | A01G 7/06 514/616 |
| 2015/0150247 A1 | * | 6/2015 | Wacker .................. | A01N 39/04 504/127 |

FOREIGN PATENT DOCUMENTS

| | | | |
|---|---|---|---|
| EP | 2421372 | * | 5/2013 |
| WO | WO 2013113498 | * | 8/2013 |

* cited by examiner

*Primary Examiner* — Mina Haghighatian
(74) *Attorney, Agent, or Firm* — Yancy IP Law, PLLC

(57) ABSTRACT

The present invention relates to an herbicidal composition particularly stable at lower temperatures. The present invention provides a stable herbicidal composition comprising at least one pesticide in its salt form and a crystal habit modifying system comprising an alkoxylated alcohol and a polymer. Further the invention relates to a stable herbicidal composition comprising at least two pesticides in their salt form and a crystal habit modifying system comprising an alkoxylated alcohol and a polymer.

14 Claims, No Drawings

STABLE AQUEOUS COMPOSITIONS

CROSS-REFERENCE TO RELATED APPLICATIONS

This application claims the benefit, under 35 U.S.C. 199(e), of U.S. Provisional Application No. 62/114,325 filed on Feb. 10, 2015, the contents of which are incorporated herein by reference.

BACKGROUND OF THE INVENTION

Pesticides can be formulated in the form of solid or liquid formulation. Solid formulation include dry flowables (DF), granules, wettable powders, soluble granules, water dispersible granules, effervescent granules and so on. Liquid formulation include soluble concentrates, suspension concentrates, emulsifiable concentrates, micro-emulsion, oil based suspension concentrate or suspoemulsion and so on. Type or nature of the active ingredient is very important in deciding the type of liquid formulation. Water soluble active ingredients are formulated as soluble concentrates (SL) and water insoluble active ingredients are formulated in the form of suspension concentrates (SC). For a combination of water soluble active ingredient and a water insoluble active ingredient the preferred formulation type is suspoemulsion or microemulsion.

Water soluble active ingredients include the active ingredients which are capable of forming a salt. If the active ingredient has an acid group, for example a carboxylic acid group (COOH), sulfonic acid group ($-SO_3H$) or phenolic group (—OH), they can form a salt with counter ions of alkali metals like calcium, magnesium or with counter ions of ammonia, alkyl amine, dialkyl amine or trialkyl amine. If the active ingredient has a basic group like an amine or a substituted amine it can form a salt with counter ion like hydrogen, a carboxylate, a sulfonate or a phosphate compound.

The liquid formulations in the form of soluble concentrate are clear solution dissolved in it is the water soluble active ingredient in the form of salt and other soluble surfactants and/or organic solvents. This formulation may contain a co-solvent to maintain homogeneity of the formulation. These formulations often suffer from a drawback as they tend to solidify as the storage temperature decreases. It is understood that when the active ingredients and/or adjuvants are solids at room temperature, at lower temperatures, their aqueous formulations have the tendency for crystallisation of the solids present in it. Such formulations when stored under cooler climatic conditions require further warming up of the formulation to make it homogenous to enable further use. These procedures are often unsafe and may affect the bioefficacy of the product. There can be uneven phase resulting in uneven distribution of the active ingredient and the surfactant resulting into uneven, inadequate and often insufficient application of the active ingredient resulting into ineffectiveness of formulation.

This problem is more aggravated when a liquid aqueous formulation contains one or more salt forming pesticides. If there is a solid separation, the formulation becomes inconsistent, non-homogenous and difficult to handle. It will also result into uneven distribution of active ingredients resulting in poor control of weeds.

Examples of such herbicides include nitrophenyl ether herbicides such as acifluorfen and benzothiadiazine herbicide such as bentazone.

Acifluorfen and its preferred derivatives are from the class of nitrophenyl ether herbicides (diphenyl ethers) and act as Protoporphyrinogen oxidase inhibitor. It is a selective contact herbicide, absorbed by the foliage and roots and is used as a post-emergence herbicide for the control of annual broad-leaved weeds (*Abutilon, Amaranthus, Datura, Euphorbia, Polygonum, Ipomoea, Xanthium* spp.), on grasses in soya beans, peanuts and rice. Usually it is applied in the form of sodium salt and is formulated as soluble concentrate which is sold under the brand 'Blazer'.

Bentazone is a selective contact herbicide, absorbed mainly by the foliage, but also by the roots. It is a photosynthetic electron transport inhibitor at the photosystem II receptor site. Bentazone is used in controlling *Anthemis, Chamomilla* and *Matricaria* spp., *Chrysanthemum segetum, Galium aparine, Lapsana communis* and *Stellaria media* in winter and spring cereals. Other crops include peanuts, maize, peas, *Phaseolus* beans, rice (*Cyperus difformis, C. esculentus, C. serotinus, Monochoria vaginalis, Sagittaria pygmaea, S. sagittifolia, Alisma* and *Commelina* spp., *Scirpus maritimus* and *S. mucronatus*) and soya beans (*Abutilon theophrasti, Capsella bursa-pastoris, Cyperus esculentus, Datura stramonium, Helianthus* spp., *Polygonum* spp., *Portulaca* spp., *Sida spinosa, Ambrosia* spp., *Sinapis arvensis* and *Xanthium* spp.).

Combinations of particular interest are that of acifluorfen and bentazone as their activity is complementary—an effective control of most of the weeds can be achieved. Usually acifluorfen is applied in the form of sodium salt and is formulated as soluble concentrate which has a freezing point of 5° C. Since the freezing point is on a higher side, precaution has to be taken while making the formulation as it leads to crystallisation of solid (or freezing of solution) between 10-0° C. This problem aggravates when acifluorfen is required to be used in combination with other active ingredients. For example, when acifluorfen is combined with another salt solution of bentazone a significant problem normally occurs. The problem is the sedimentation or tendency for crystallisation of the active ingredients at lower temperatures. Antifreeze agents/crystal inhibitors are generally used to solve the problem of solidification at low temperature. Generally used antifreeze agents include glycols like propylene glycol, and crystal inhibitors include Rhodafac rs-610, K: Atlox AL-3382 and Agsole Ex.

'Galaxy' and 'Storm' are the two commercially available compositions containing acifluorfen sodium and bentazone sodium. However both the formulations fail the freeze thaw test meaning that both the formulations are suffering from the problem of solidification at low temperatures.

It has been observed by the inventors of the present invention that while using known antifreeze agents such as glycol and glycol based solvents alone could not solve the problem of low temperature stability. It has also been noted by the present inventors that use of known thickening agents also leads to solidification problems. Additionally, the known thickening agents led to high viscous aqueous concentrates which were creating difficulties in pouring and/or pumping the formulation in the field especially at low temperatures. These formulations when applied in the field may lead to uneven distribution of the active ingredients resulting in poor bioefficacy.

It would therefore be highly desirable to have aqueous based formulations which are stable especially at low temperatures.

Inventors of the present invention have surprisingly found out that a stable liquid composition of pesticides in their salt form can be prepared by way of adding a crystal habit modifying system.

SUMMARY OF THE INVENTION

The present invention relates to a liquid pesticide composition comprising at least one pesticide in its salt form and a crystal habit modifying system comprising an alkoxylated alcohol and a polymer which exhibit excellent low temperature storage stability.

Further the invention relates to a liquid herbicidal composition comprising at least two pesticides in their salt form and a crystal habit modifying system comprising an alkoxylated alcohol and a polymer.

The invention further provides a process for the preparation of a liquid pesticide composition comprising at least one pesticide in its salt form and a crystal habit modifying system comprising an alkoxylated alcohol and a polymer which exhibit excellent low temperature storage stability.

The invention further provides a process for the preparation of a liquid pesticide composition comprising at least two pesticides in their salt form and a crystal habit modifying system comprising an alkoxylated alcohol and a polymer which exhibit excellent low temperature storage stability.

In another aspect the invention relates to the use of a composition comprising a pesticide in its salt form and a crystal habit modifying system comprising an alkoxylated alcohol and a polymer for effectively controlling undesired plants.

In another aspect the invention relates to the use of a composition comprising at least two pesticides in their salt form and a crystal habit modifying system comprising an alkoxylated alcohol and a polymer for effectively controlling undesired plants.

OBJECTS OF THE INVENTION

It is an object of the present invention to provide herbicidal compositions comprising at least one pesticide in its salt form which is stable at low temperatures.

It is an object of the present invention to provide herbicidal compositions comprising at least two pesticides in their salt form which is stable at low temperatures.

It is another object of the present invention to provide a liquid herbicidal composition comprising at least two pesticides in their salt form which is stable at low temperatures.

Another object of the present invention is to provide a process for herbicidal compositions comprising at least two pesticides in their salt form which is stable at low temperatures.

DETAILED DESCRIPTION

Present invention is related to herbicidal compositions comprising at least one pesticide in its salt form which demonstrate excellent stability at low temperature and are bioefficacious. The present invention particularly relates to liquid compositions comprising at least two pesticides in their salt form and a crystal habit modifying system comprising an alkoxylated alcohol and a polymer which are stable at temperatures.

Several viscosity modifiers are known to be used for various aqueous based agrochemical formulations. However, formulations suffer from the drawback of low temperature stability especially when using pesticide in its salt form active ingredients which are prone to solidify at low temperature. The formulations are either cloudy or have crystal formation or have solid separation when they are tested for stability at temperature below 0° C.

Although the formulations are said to be bioefficacious in controlling weed, they are not practicable due to low temperature instability.

Inventors of the present invention surprisingly found out that the problem of low temperature stability of such pesticides in their salt form can be overcome by using a crystal habit modifying system comprising an alkoxylated alcohol and a polymer.

Accordingly there is provided a crystal habit modifying system comprising an alkoxylated alcohol and a polymer for stabilizing pesticidal salt solutions at low temperatures.

In an embodiment of the present invention there is provided a composition comprising at least one pesticide in its salt form and a crystal habit modifying system comprising an alkoxylated alcohol and a polymer which exhibit excellent low temperature storage stability.

In another embodiment there is provided a liquid herbicidal composition comprising at least two pesticides in their salt form and a crystal habit modifying system comprising an alkoxylated alcohol and a polymer.

Low temperatures according to the present invention refer to a temperature below 10° C., preferably below 5° C., more preferable below 0° C., and most preferably it is −10° C.

According to another embodiment of the present invention the crystal habit modifying system comprises an alkoxylated alcohol and a polymer.

In a preferred embodiment the alkoxylated alcohol is selected from ethylene glycol, propylene glycol and butyl cellosolve.

According to yet another preferred embodiment the alkoxylated alcohol is butyl cellosolve.

In another embodiment of the present invention, the composition comprises from about 0.1 to 25% by weight of the alkoxylated alcohol preferably from about 1% to about 15% and more preferably from about 1% to about 10% by weight of the formulation.

According to another embodiment of the present invention, the polymer is a crystal growth inhibitor, a viscosity modifier, crystal growth regulator, structuring agent or a rheology modifier.

Examples of polymers include but not limited to modified cellulose derivatives, their co-polymers, modified starches, polyvinyl alcohols and derivatives, esters of alkoxylated polyols, clays, modified silica and natural gums such as guar gum, xanthan gum, HP guar, gelatin, dextrin, collagen and derivatives.

According to a preferred embodiment of the present invention the thickener is selected from the group consisting of xanthan gum, guar gum, HP guar, hydroxyl ethyl cellulose and esters of alkoxylated polyols.

In an embodiment of the present invention, the composition comprises from about 0.01% to about 0.2% by weight of the thickener preferably from about 0.05% to about 0.18% by weight of the formulation.

According to an embodiment of the present invention, the composition may comprise at least one pesticide in its salt form selected from various classes of pesticides.

In an embodiment of the present invention, the composition comprises at least one pesticide in its salt form selected from nitrophenyl ether herbicides, organophosphorus herbicides or benzothiadiazine herbicide.

In another embodiment of the present invention the nitrophenyl ether herbicide is selected from acifluorfen, aclonifen, bifenox, chlomethoxyfen, chlornitrofen, etnipromid, fluorodifen, fluoroglycofen, fluoronitrofen, fomesafen, fucaomi, furyloxyfen, halosafen, lactofen nitrofen, nitrofluorfen and oxyfluorfen.

In an embodiment of the present invention the organophosphorus herbicide is selected from amiprofos-methyl, amiprophos, anilofos, bensulide, bilanafos, butamifos, clacyfos, fosamine, glufosinate, glufosinate-P, glyphosate and piperophos.

In another embodiment of the present invention the benzothiadiazine herbicide is bentazone.

According to another embodiment of the present invention the preferred nitrophenyl ether herbicide is acifluorfen.

In another embodiment of the present invention, there is provided a combination of at least two pesticides in their salt form.

In an embodiment of the present invention, the combination of two pesticides in their salt form comprises nitrophenyl ether herbicides and benzothiadiazine herbicides.

According to another embodiment of the present invention, the two pesticides in their salt form are acifluorfen and bentazone.

In an embodiment of the present invention the composition comprises from about 0.1% to about 30% by weight of nitrophenyl ether herbicide preferably from about 1% to about 25% by weight of the formulation.

In another embodiment of the present invention, the composition comprises from about 0.1% to about 60% by weight of benzothiadiazine herbicide preferably from about 1% to about 50% by weight of the formulation.

In an embodiment of the present invention there is provided a composition comprising acifluorfen, bentazone and a crystal habit modifying system wherein the crystal habit modifying system comprises butyl cellosolve and hydroxyethyl cellulose.

The composition comprises from about 1% to about 25% by weight of acifluorfen, from about 1% to about 50% by weight of bentazone, from about 1% to about 15% by weight of butyl cellosolve and from about 0.01% to about 0.2% by weight of hydroxyethyl cellulose.

In another embodiment of the present invention, there is provided a composition comprising acifluorfen, bentazone and a crystal habit modifying system wherein the crystal habit modifying system comprises butyl cellosolve and esters of alkoxylated polyols.

The composition comprises from about 1% to about 25% by weight of acifluorfen, from about 1% to about 50% by weight of bentazone, from about 1% to about 15% by weight of butyl cellosolve and from about 0.01% to about 0.2% by weight of esters of alkoxylated polyols.

In yet another embodiment of the present invention, there is provided a composition comprising acifluorfen, bentazone and a crystal habit modifying system wherein the crystal habit modifying system comprises butyl cellosolve and xanthan gum.

The composition comprises from about 1% to about 25% by weight of acifluorfen, from about 1% to about 50% by weight of bentazone, from about 1% to about 15% by weight of butyl cellosolve and from about 0.05% to about 0.2% by weight of xanthan gum.

According to an embodiment of the present invention, there is provided a composition comprising acifluorfen, bentazone and a crystal habit modifying system wherein the crystal habit modifying system comprises butyl cellosolve and guar gum.

The composition comprises from about 1% to about 25% by weight of acifluorfen, from about 1% to about 50% by weight of bentazone, from about 1% to about 15% by weight of butyl cellosolve and from about 0.05% to about 0.2% by weight of guar gum.

According to an embodiment of the present invention, there is provided a composition comprising acifluorfen, bentazone and a crystal habit modifying system wherein the crystal habit modifying system comprises butyl cellosolve and HP guar.

The composition comprises from about 1% to about 25% by weight of acifluorfen, from about 1% to about 50% by weight of bentazone, from about 1% to about 15% by weight of butyl cellosolve and from about 0.05% to about 0.2% by weight of HP guar.

In an embodiment of the present invention there is provided a composition comprising glufosinate, glyphosate and a crystal habit modifying system wherein the crystal habit modifying system comprises butyl cellosolve and esters of alkoxylated polyols.

The composition comprises from about 1% to about 35% by weight of glufosinate, from about 1% to about 50% by weight of glyphosate, from about 1% to about 15% by weight of butyl cellosolve and from about 0.05% to about 0.2% by weight of esters of alkoxylated polyols.

The aqueous compositions according to the present invention may further comprise other agronomically suitable excipients such as surfactants, solvent, fertilizer, pH modifiers, suspending agents, spray droplet modifiers, pigments, antioxidants, foaming agents, light-blocking agents, compatibilizing agents, antifoam agents, sequestering agents, neutralizing agents, corrosion inhibitors, dyes, odorants, spreading agents, penetration aids, micronutrients, emollients, lubricants, sticking agents, dispersing agents, antimicrobial agents, and the like. In an embodiment of the present invention, the surfactants may be selected from nonionic surfactants. Examples of nonionic surfactants are: fatty alcohols having 10-24 carbon atoms with 0-60 EO and/or 0-20 PO and/or 0-15 BO in any order; fatty acid alkoxylates and triglyceride alkoxylates; fatty acid amide alkoxylates; alkylene oxide adducts of alkynediols; sugar derivatives such as amino sugars and amido sugars; polyacrylic and polymethacrylic derivatives; polyamides such as modified gelatins or derivatized polyaspartic acid; surfactant polyvinyl compounds such as modified PVP; polyol-based alkylene oxide adducts; polyglycerides and derivatives thereof.

The process for preparing compositions according to the present invention is not particularly limiting. The salts of active ingredients are prepared according to processes known in the art.

According to a preferred embodiment of the present invention, the composition was prepared as follows:

The active ingredients was mixed in an empty reactor with calculated amounts of water and sodium hydroxide under stirring and heated to 75° C. The temperature was maintained at 75° C. for 24 hours. The reaction mixture was cooled to 35° C. and then charged butyl cellosolve and hydroxyethyl cellulose along with other customary adjuvants. Stirred for 1 hour, and was filtered.

In an embodiment of the present invention there is provided a method to control unwanted plants or to influence the growth of plants by treating said plants in the field with a composition comprising at least one pesticide in its salt form and a crystal habit modifying system comprising an alkoxylated alcohol and a polymer.

The invention shall now be described with reference to the following specific examples. It should be noted that the examples appended below illustrate rather than limit the invention and that those skilled in the art will be able to design many alternative embodiments without departing from the scope of the present invention. The formulation obtained is clear and no haziness or solidification is observed at 54° C., 25° C., 14° C. and 0° C. after 7/14 days as per CIPAC guidelines (MT 39.3), indicating that the composition is stable. Sub-zero stability test has been checked by keeping samples at −10° C. for 14 days.

EXAMPLES

Example 1

A composition of acifluorfen sodium according to the present invention was prepared as follows:

| Ingredients | % (w/w) |
| --- | --- |
| Aciflourfen sodium | 20.1 |
| Butyl celloslove | 8.5 |

| Ingredients | % (w/w) |
| --- | --- |
| HP guar | 0.1 |
| Water | q.s |

The composition was prepared by the following manner:

Aciflourfen sodium was mixed in an empty rector with butyl cellosolve, HP guar and other adjuvants in required quantity. The mixture was stirred for an hour and then filtered.

Example 2

A composition of acifluorfen sodium and bentazone sodium according to the present invention was prepared as follows:

| Ingredients | % (w/w) |
| --- | --- |
| Aciflourfen sodium | 13.4 |
| Benatazone sodium | 29.2 |
| Butyl celloslove | 6.0 |
| Esters of alkoxylated polyols | 0.15 |
| Nonionic surfactant | 5.0 |
| Water | q.s |

Example 3

A composition of glufosinate ammonium and glyphosate isopropyl amine salt according to the present invention was prepared as follows:

| Ingredients | % (w/w) |
| --- | --- |
| Glufosinate ammonium | 16.0 |
| glyphosate isopropyl amine salt | 20.2 |
| Butyl celloslove | 6.0 |
| Esters of alkoxylated polyols | 0.15 |
| Nonionic surfactant | 5.0 |
| Water | q.s |

The stability studies of the compositions are illustrated in Tables 1-4.

TABLE 1

| Composition sample no | Active ingredient in salt form | % by weight | Alkoxylated alcohol % by weight | Polymer/crystal inhibitor % by weight | Observation at ambient temp. | Observation at 10°-0° C. | Observation below 0° C. (up to −10° C.) |
| --- | --- | --- | --- | --- | --- | --- | --- |
| 1 | A | 20.1 | C-8.5 | 0.0 | clear | hazy | crystal |
| 2 | B | 44 | C-8.5 | 0.0 | clear | hazy | crystal |
| 3 | A:B | 13.4:29.2 | C-1.5 | 0.0 | clear | crystal | crystal |
| 4 | A:B | 13.4:29.2 | C-5 | 0.0 | clear | crystal | crystal |
| 5 | A:B | 13.4:29.2 | C-12 | 0.0 | hazy | crystal | crystal |
| 6 | A:B | 13.4:29.2 | C-15 | 0.0 | Layer separation | — | — |

A: acifluorfen,
B: bentazone,

C: butyl cellosolve

From the above table it has been found that though the compositions were stable at ambient temperatures, they failed at low temperatures.

TABLE 2

| Composition sample no | Active ingredient in salt form | % by weight | Alkoxylated alcohol % by weight | Crystal inhibitor % by weight | Observation at ambient temp. | Observation at 10°-0° C. | Observation below 0° C. (up to −10° C.) |
|---|---|---|---|---|---|---|---|
| 1 | A:B | 13.9:30.0 | C:D-0:6.5 | 0.0 | clear | crystal | crystal |
| 2 | A:B | 13.9:30.0 | C:E-0:5.0 | 0.0 | clear | crystal | crystal |
| 3 | A:B | 13.9:30.0 | C:E - 3.0:5.0 | 0.0 | clear | crystal | crystal |
| 4 | A:B | 13.9:30.0 | C-1.5 | H: 0.3 | clear | crystal | crystal |
| 5 | A:B | 13.9:30.0 | C:I - 1.5:4.0 | J: 0.2 | clear | crystal | crystal |
| 6 | A:B | 13.9:30.0 | C:I - 1.5:4.0 | K: 0.2 | clear | crystal | crystal |

A: acifluorfen,
B: bentazone,
C: butyl cellosolve,
D: propylene glycol,
E: Ethylene glycol,
H: Agsole Ex,
I: tetrahydrofurfuryl alcohol,
J: Rhodafac rs-610,
K: Atlox AL-3382

It has been noted by the inventors of the present invention that compositions comprising alkoxylated alcohols, known antifreeze agents and/or known crystal inhibitors, crystal formation was observed at or below 0° C. as evident from table 2.

TABLE 3

| Composition sample no | Active ingredient in salt form | % by weight | Alkoxylated alcohol % by weight | Crystal inhibitor % by weight | Observation at ambient temp. | Observation at 10°-0° C. | Observation below 0° C. (up to −10° C.) |
|---|---|---|---|---|---|---|---|
| 1 | A | 20.1 | 0.0 | H-0.2 | clear | crystal | crystal |
| 2 | B | 44 | 0.0 | J-0.2 | clear | crystal | crystal |
| 3 | A:B | 13.9:30.0 | 0.0 | H-0.2 | clear | crystal | crystal |
| 4 | A:B | 13.9:30.0 | 0.0 | J-0.2 | clear | crystal | crystal |

A: acifluorfen,
B: bentazone,
H: Agsole Ex,
J: Rhodafac rs-610,
K: Atlox AL-3382

It has further been further noted by the inventors of the present invention that compositions comprising the known crystal inhibitors were not solving the problem of low temperature stability as crystal formation was observed at low temperatures as evident from table 3.

TABLE 4

| Composition sample no | Active ingredient in salt form | % by weight | Alkoxylated alcohol % by weight | Polymer % by weight | Observation at ambient temp. | Observation at 10°-0° C. | Observation below 0° C. (up to −10° C.) |
|---|---|---|---|---|---|---|---|
| 1 | A | 20.1 | C-8.5 | F-0.1 | clear | clear | clear |
| 2 | B | 44 | C-9 | L-0.1 | clear | clear | clear |
| 3 | A:B | 13.4:29.2 | C-6.0 | L-0.15 | clear | clear | clear |
| 4 | A:B | 13.4:29.2 | C-6.0 | G-0.2 | clear | clear | clear |
| 5 | A:B | 8.0:36.0 | C-5.0 | G-0.15 | clear | clear | clear |
| 6 | A:B | 6.4:30.6 | C-6.0 | G-0.10 | clear | clear | clear |
| 7 | A:B | 13.4:29.2 | C-5.0 | G-0.05 | clear | clear | hazy |
| 8 | A:B | 13.4:29.2 | C-5.0 | F-0.2 | clear | clear | clear |
| 9 | A1:B1 | 16.0:20.2 | C-6.0 | L-0.15 | clear | clear | clear |

A: acifluorfen,
B: bentazone,
A1: glufosinate ammonium,
B1: Glyphosate isopropyl amine salt,
C: butyl cellosolve,
F: HP guar,
G: Hydroxy ethyl cellulose, TABLE 4-continued

| Composition sample no | Active ingredient in salt form | % by weight | Alkoxylated alcohol % by weight | Polymer % by weight | Observation at ambient temp. | Observation at 10°-0° C. | Observation below 0° C. (up to −10° C.) |
|---|---|---|---|---|---|---|---|

L: esters of alkoxylated polyols

As table 4 indicates inventors of the present invention found out that low temperature stability of aqueous formulation of a pesticide in its salt form or combination of two such active ingredients can be achieved by using a crystal habit modifying system comprising an alkoxylated alcohol and a polymer. Samples were found to be stable at temperatures up to −10° C. It was further noted that in case of sample no. 7 wherein the amount of polymer was very low, the sample appeared to be hazy at −10° C.

Although the present invention has been disclosed in terms of a preferred embodiment, it will be understood that numerous additional modifications and variations could be meet thereto without departing from the scope of the invention as defined by the following claims:

We claim:

1. A stable aqueous composition comprising,
   at least one herbicide in its salt form, wherein said herbicide is selected from the group consisting of acifluorfen, bentazone, and combinations thereof as the only herbicidal active ingredients in said composition and
   a crystal habit modifying system comprising an alkoxylated alcohol and a polymer, wherein the alkoxylated alcohol is butyl cellosolve; and wherein the polymer is selected from esters of polyalkoxylated alcohols, guar gum, xanthan gum, HP guar, and hydroxyethyl cellulose; wherein said polymer is present in an amount from about 0.1 to about 0.2% by weight of the composition;
   wherein said composition is stable at −10° C.

2. The composition of claim 1 comprising both acifluorfen and bentazone salts.

3. The composition of claim 2 comprising 1-25 wt. % acifluorfen salt and 1-50 wt. % bentazone salt based on the total weight of the composition.

4. The composition of claim 3 comprising 6-14 wt. % acifluorfen salt and 29-36 wt. % bentazone salt based on the total weight of the composition.

5. The composition of claim 1 wherein said composition includes 1-15 wt. % of said butyl cellosolve based on the total weight of the composition.

6. The composition of claim 5 wherein said composition includes 5-10 wt. % butyl cellosolve based on the total weight of the composition.

7. A method of controlling weeds said method comprising applying to a plant or a plant locus said stable aqueous composition of claim 1.

8. A stable aqueous composition comprising,
   1-25 wt. % acifluorfen salt and 1-50 wt. % bentazone salt based on the total weight of the composition as the only herbicidal active ingredients in said composition and
   a crystal habit modifying system comprising an alkoxylated alcohol and a polymer, wherein the alkoxylated alcohol is butyl cellosolve; and wherein the polymer is selected from the group consisting of esters of polyalkoxylated alcohols, HP guar, and hydroxyethyl cellulose; wherein said polymer is present in an amount from about 0.1 to about 0.2% by weight of the composition; and wherein said composition includes 1-15 wt. % of said butyl cellosolve based on the total weight of the composition;
   wherein said composition is stable at −10° C.

9. The composition of claim 8, wherein said composition includes 6-14 wt. % acifluorfen salt, 29-36 wt. % bentazone salt, and 5-10 wt. % butyl cellosolve based on the total weight of the composition.

10. A stable aqueous composition consisting of,
    at least one herbicide in its salt form, wherein said herbicide is selected from the group consisting of acifluorfen, bentazone, and combinations thereof as the only herbicidal active ingredients in said composition and
    a crystal habit modifying system consisting of an alkoxylated alcohol and a polymer, wherein the alkoxylated alcohol is butyl cellosolve; and wherein the polymer is selected from esters of polyalkoxylated alcohols, guar gum, xanthan gum, HP guar, and hydroxyethyl cellulose; wherein said polymer is present in an amount from about 0.1 to about 0.2% by weight of the composition;
    water; and
    optionally at least one surfactant,
    wherein said composition is stable at −10° C.

11. The composition of claim 10, wherein said optional surfactant is a nonionic surfactant.

12. The composition of claim 11, wherein said nonionic surfactant is selected from the group consisting of fatty alcohols having 10-24 carbon atoms; fatty acid alkoxylates; triglyceride alkoxylates; fatty acid amide alkoxylates; alkylene oxide adducts of alkynediols; sugar derivatives; amino sugars; amido sugars; polyacrylic derivatives; polymethacrylic derivatives; polyamides; modified gelatins; derivatized polyaspartic acid; surfactant polyvinyl compounds; modified PVP; polyol-based alkylene oxide adducts; polyglycerides and derivatives thereof.

13. The composition of claim 11 consisting of 1-25 wt. % acifluorfen salt and 1-50 wt. % bentazone salt based on the total weight of the composition.

14. The composition of claim 11 consisting of 1-15 wt. % of said butyl cellosolve based on the total weight of the composition.

* * * * *